(12) United States Patent
Amoyal et al.

(10) Patent No.: US 11,166,879 B2
(45) Date of Patent: Nov. 9, 2021

(54) TAMPER-RESISTANT CONTAINER WITH UNIQUE IDENTITY AUTHENTICATION AND NETWORK-ENABLED SECURITY FEATURES

(71) Applicant: Impruvon, inc., King George, VA (US)

(72) Inventors: Justin Michael Amoyal, Ashburn, VA (US); Michael Jared Mazzocco, King George, VA (US)

(73) Assignee: Impruvon, Inc., King George, VA (US)

( * ) Notice: Subject to any disclaimer, the term of this patent is extended or adjusted under 35 U.S.C. 154(b) by 0 days.

(21) Appl. No.: 16/923,641

(22) Filed: Jul. 8, 2020

(65) Prior Publication Data

US 2021/0007937 A1     Jan. 14, 2021

Related U.S. Application Data

(60) Provisional application No. 62/871,426, filed on Jul. 8, 2019.

(51) Int. Cl.
*A61J 7/04*     (2006.01)
*A61J 7/00*     (2006.01)
(Continued)

(52) U.S. Cl.
CPC .............. *A61J 7/0427* (2015.05); *A61J 1/03* (2013.01); *A61J 7/0076* (2013.01); *A61J 7/0418* (2015.05);
(Continued)

(58) Field of Classification Search
CPC .......... A61J 7/0427; A61J 7/0076; A61J 1/03; A61J 7/0418; A61J 7/0481;
(Continued)

(56) References Cited

U.S. PATENT DOCUMENTS

| 5,478,586 A | 12/1995 | Connor |
| 6,422,133 B1 | 7/2002 | Brady |

(Continued)

*Primary Examiner* — Michael Collins
(74) *Attorney, Agent, or Firm* — Offit Kurman, P.A.; Steven Scott Lloyd

(57) ABSTRACT

The present invention is that of a tamper-resistant container of durable material and structure. In certain embodiments, the container is configured to include power source, such as a battery rechargeable via provided uniform serial bus (USB) port, which powers a unique user identity authentication sensor, such as a fingerprint scanner, in combination with a vibration sensor to detect movement. The user identity authentication and vibration sensors communicate with a provided computer software application via application program interface such as may be installed on a computer, preferably a smartphone. Short message service (SMS) text messages may provide tamper alerts, and a system comprising the software application may enable remote locking and unlocking, access and approval, as well as updates and reminders related to the administration of contents such as prescription medications. The methods disclosed herein provide for secure access to medications, temper prevention and improved compliance, tracking and data collection.

17 Claims, 8 Drawing Sheets

(51) Int. Cl.
*A61J 1/03* (2006.01)
*H04M 1/725* (2021.01)
*H04L 29/08* (2006.01)
*H04W 4/80* (2018.01)
*G07C 9/00* (2020.01)
*G16H 20/13* (2018.01)
*H04M 1/72406* (2021.01)
*G06K 9/00* (2006.01)

(52) U.S. Cl.
CPC ........ *A61J 7/0481* (2013.01); *G07C 9/00563* (2013.01); *G16H 20/13* (2018.01); *H04L 67/025* (2013.01); *H04L 67/2809* (2013.01); *H04M 1/72406* (2021.01); *H04W 4/80* (2018.02); *G06K 9/00087* (2013.01)

(58) Field of Classification Search
CPC .... H04L 67/2809; H04L 67/025; H04W 4/80; G07C 9/00563; G16H 20/13; H04M 1/72406; G06K 9/00087

USPC ................................................. 700/231–244
See application file for complete search history.

(56) References Cited

U.S. PATENT DOCUMENTS

| | | | |
|---|---|---|---|
| 6,797,304 B2 | 9/2004 | McGonagle | |
| 7,040,218 B1 | 5/2006 | Biolchini, Jr. | |
| 7,194,951 B1 | 3/2007 | Porter | |
| 10,355,730 B1* | 7/2019 | Zalewski | H04B 1/3833 |
| 2014/0278508 A1* | 9/2014 | Akdogan | A61J 7/02 |
| | | | 705/2 |
| 2014/0309772 A1* | 10/2014 | Shen | A61J 7/0481 |
| | | | 700/237 |
| 2017/0109498 A1* | 4/2017 | Childress | G16H 40/67 |
| 2019/0378602 A1* | 12/2019 | LaTorraca | G16H 40/00 |
| 2019/0392934 A1* | 12/2019 | Tabakin | G16H 10/60 |
| 2020/0345587 A1* | 11/2020 | Aon | A61J 7/0481 |

* cited by examiner

TAMPER-RESISTANT CONTAINER WITH UNIQUE IDENTITY AUTHENTICATION AND NETWORK-ENABLED SECURITY FEATURES

CROSS-REFERENCE TO RELATED APPLICATIONS

The present application claims priority to and the benefit of U.S. Prov. App. No. 62/871,426, filed Jul. 9, 2019, the content of which is hereby incorporated by reference in its entirety.

STATEMENT REGARDING FEDERALLY SPONSORED RESEARCH OR DEVELOPMENT

The invention described herein was made without federal funding.

BACKGROUND OF THE INVENTION

The present invention is in the technical field of containers for medicines, representing an alternatives to conventional medicine pill bottles, cases and lids. More particularly, the present invention is in the technical field of dispensers of medicine, such as pill bottles, cases and lids that are tamper resistant, require a unique identification to authenticate the identity of the user and enable mobile locking, unlocking and alarming that assimilates with text messaging and modern computing capabilities, such as smartphone capabilities, via a software application and application program interface (API). The field also encompasses organizers of medicines that aid in compliance with schedules of administration of the medicines contained therein. These tamper-resistant containers may also be configured with audio or visual alarms to alert users of unauthorized attempts to access the contents and cameras for verifying compliance.

Existing conventional pill bottles, cases and lids are generally not fabricated from a hardened material with mobile locking, unlocking and alarming capabilities, and are not accompanied with unique user identity authentication. Generally speaking, the patient or other user must open a childproof pill lid, for example, to gain access to the medication inside the bottle or case. With conventional pill bottles, cases and lids, the patient's medication is vulnerable to being stolen, moved, tampered with and not completely secured, and provides no mechanism to alert the patient or a patient custodian if tampering occurs. It is thus an object of the invention of the present disclosure to provide a secure, tamper-resistant container of superior material to the state of the art that leverages cloud computing and mobile software application technologies to prevent unauthorized access to medications and alert users when attempts at such unauthorized access are made, as well as provide a mobile means of locking and unlocking containers of medicine. It is another object of the invention to improve the tracking of medication administration, adherence, and logging histories for users and caregivers. It is a further object of the invention to provide repetition, routine and rewards in the forms of games, avatars and the like visible on a graphical user interface (GUI) to encourage patients suffering from disabilities such as autism, Alzheimer's disease, dementia or other similar disabilities affecting compliance to take the appropriate doses of necessary medications timely, and also alert patients and caregivers as to when medications are expired and should be replaced. In certain embodiments, the invention of the present disclosure may be used to support medication adherence support and the training of patients to become independent in their adherence to medication schedules and special requirements such as coadministration with food or warnings against driving or operating heavy equipment following administration.

The invention also relates to the field of medical record-keeping with regard to the impact of medications on patients. Unlike current methods, users and caregivers may be prompted at each medication event to input data related to the positive and negative observations, including but not limited to observations of side effects of the medication administered. It is an object of the present invention to save, compile, and analyze this data in order to drive insights related to which medications are successful, unsuccessful, or have potentially undesirable side effects. Such data can then be analyzed in combination with the user data collected using the system to gain previously unavailable insights on the impacts various medications on people with preexisting conditions or chronic illnesses, for example.

SUMMARY OF THE INVENTION

The present invention is that of tamper-resistant containers of resilient material in the form of pill bottles, cases and lids. In one aspect, containers according to the present invention are fabricated from more durable, tamper-resistant materials than what is currently available. A container according to the present disclosure may also be configured with a power source, such but not limited to a rechargeable battery with a universal serial bus (USB) port, that powers a unique user identity authentication sensor, such as but not limited to a fingerprint scanner, in combination with a vibration sensor to detect container movement. The user identity authentication and vibration sensors may communicate via Bluetooth or similarly transceiver to a computing device such but not limited to a smartphone or via an available wireless network to a cloud server comprising software program instructions which when executed by a processor cause the processor to process the data inputs for authentication or transmit alerts to untimely or unauthorized access to a smartphone configured to receive messages on a GUI or via short message service (SMS) text in communication with the cloud server via wireless network. In certain embodiments, a container may also be configured with a camera that allows a caregiver to see a patient taking a medicine in compliance with the appropriate schedule or an individual attempting unauthorized access.

For example, and not by way of limitation, a smartphone may receive text messages and audio or visual alerts, and may be configured to enable authenticated, remote locking or unlocking of an associated container or enable other users, such as prescribing physicians, to receive notifications related to the administration of the prescribed medications. A system of the present disclosure may also enable updates and reminders to be sent to a smartphone or other computing device regarding dosing times, the need for refills, and changes to dosing regimens. These features provide the following benefits: (1) instantly alerting of parents, friends or loved ones of unauthorized users attempting to steal pills; (2) simplification of the outdated methods of opening pill bottles and cases through access only upon authentication, such as by fingerprint reading or another suitable authentication means; and (3) eliminating unauthorized users from breaking into or cutting open pill bottles or cases to steal pills by using tough, durable manufacturing material. The alerting function as described herein may further comprise reminders to take medications and alerts when a dosage time has passed without dispensing.

This pill bottle, case and lid easily integrates with smartphones via an API installed thereon, which enables text messaging to provide users with an easy to use link for live updates and locking and unlocking of the system. A system as described herein also comprises an electronic signature capability for enabling the authenticated uploading of medication adherence data into corresponding patient medical records management systems, an improvement over current error-prone and time consuming manual processes, all while educating patients with autism and other mental disabilities of the importance of taking their medicines on time and as prescribed. These and other benefits of the invention of the present disclosure will be apparent to one of ordinary skill in the art.

DETAILED DESCRIPTION OF THE INVENTION

Figure 1:
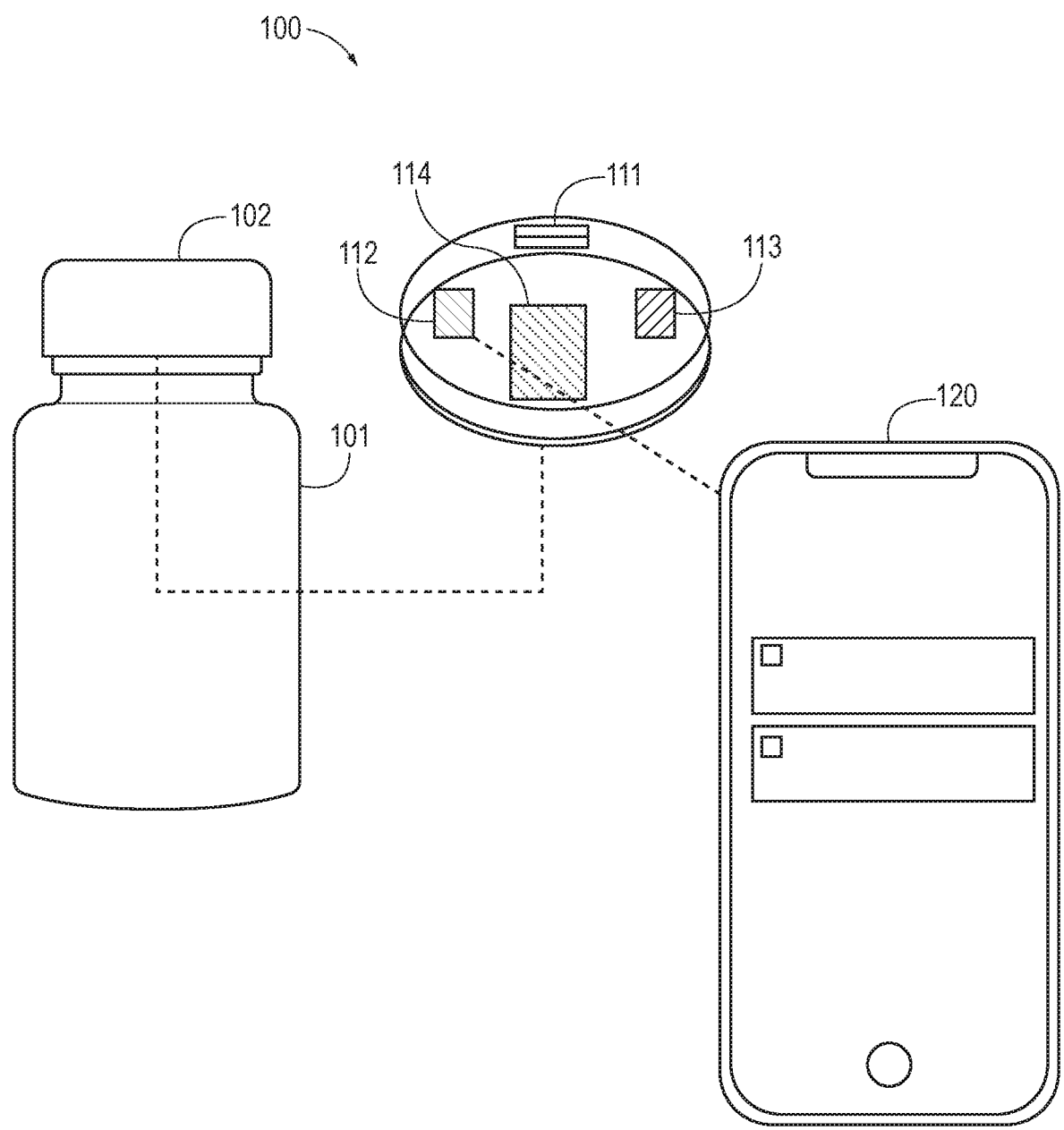
FIG. 1 is an isometric view of an exemplary embodiment of a tamper-resistant container and lid of the present invention, in communication with a smartphone.

Referring now to the invention in more detail, FIG. 1 illustrates components of a tamper-resistant container 100 according to the present invention. The illustrative embodiment of FIG. 1 comprises a bottle 101 or case suitable for containing medicine such as pills. Preferred embodiments of a tamper-resistant container as described herein may be fabricated from a more durable material than what is known in the art, such as but not limited to metal, hardened thermoplastic, fiberglass, epoxy, hardened resin and the like. The illustrative embodiment of FIG. 1 includes a lid 102 configured with a power source, such as a battery rechargeable through a USB port 111, as will be familiar to one of ordinary skill in the art, although other sources of power may be used. The container of FIG. 1 comprises a unique user identity authentication sensor, such as but not limited to a fingerprint scanner 114. The embodiment of FIG. 1 also comprises a vibration sensor 113 to detect movement of the container, and is in wireless network communication with a cloud server in further communication via a web server of the present invention to a computing device such as a smartphone 120 via an API installed on the computing device.

It is an object of the present invention to provide alerts, enable remote locking and unlocking, and communicate updates and reminders related to medication schedules, refill needs and the like. It is also an object of the invention of the present disclosure to enable the authenticated user to access medications contained inside the container only following authentication such as by fingerprint scanning. While the pill bottle, case and lid may be made of stainless steel, aluminum, or of any other sufficiently rigid and strong material such as high-strength plastic, metal, composites and the like, the various components of the pill bottle, case and lid can be made of different materials. In the embodiment of FIG. 1, the lid is also configured with a Bluetooth transceiver 112 for short wave transmission of data to a smartphone or the like in wireless network communication with a cloud server in further communication with a web server comprising a software application tangibly stored thereon which supplies instructions which when executed by a processor cause the processor to process data from the container, such as but not limited to vibration data or authentication data, and may return instructions back to the smartphone or the like for opening the container.

Figure 2:
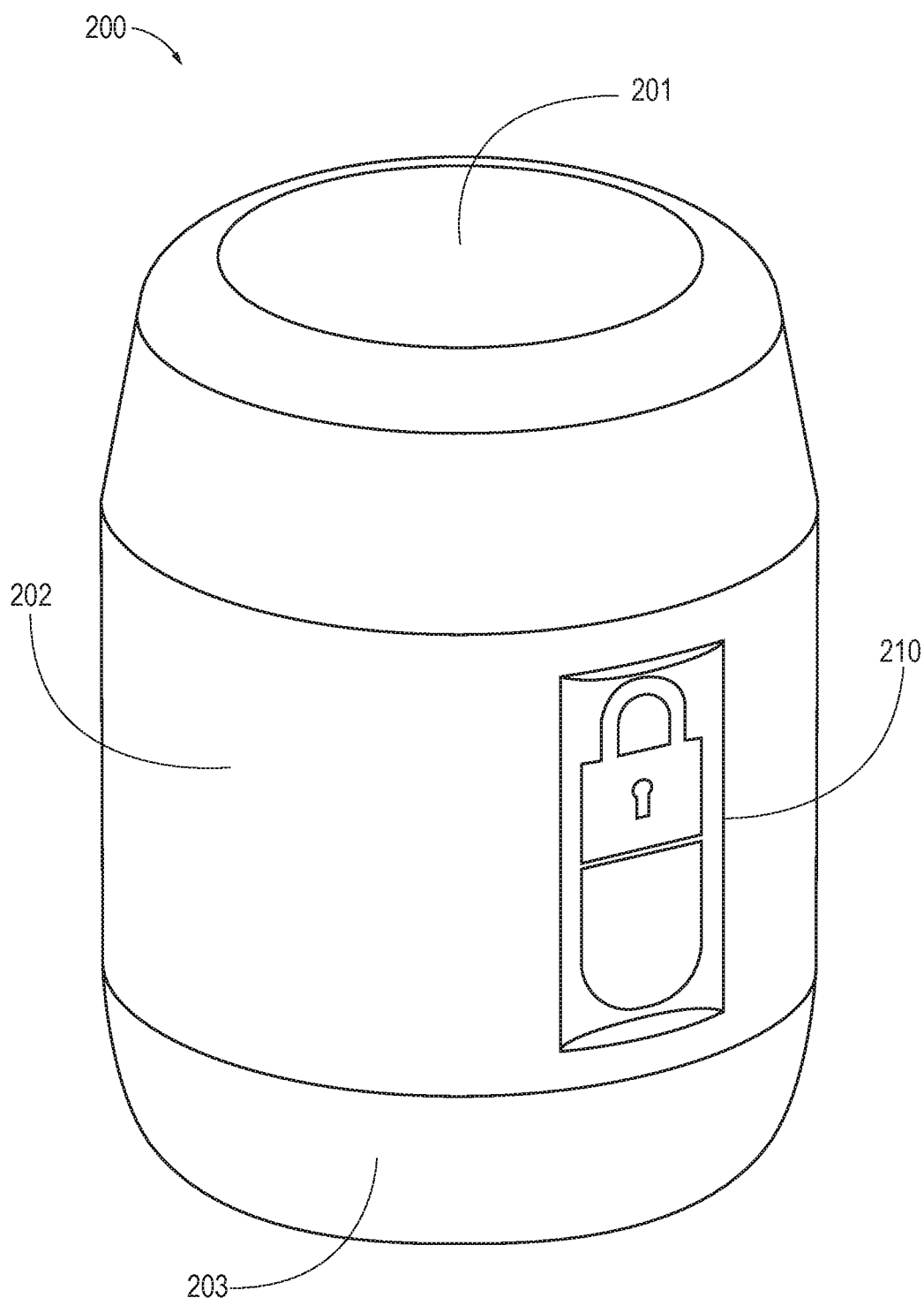
FIG. 2 is an outer perspective view of a container according to one embodiment of the present invention.

FIG. 2 illustrates the exterior of a container 200 according to the present invention. The embodiment of FIG. 2 comprises a lid 201, body 202 and base 203, the body 202 comprising a user authentication means 210 such as a fingerprint scanner for authentication of the user either automatically or by remote means, such as by signaling a custodian having a computing device in communication with a system of the present disclosure of the user authentication of a person seeking access to the medication inside for confirmation via the computing device such as a smartphone in network communication with a web server of the container. The custodian can then transmit unlocking instructions enabling the patient whose identity has been verified to access the contents needed for compliance with dosing instructions, and may be alerted by a vibration sensor of the base (not shown) in the event of an unauthorized access attempt. The embodiment of FIG. 2 may also comprise a USB charging port and Bluetooth transceiver (not shown), such as in the base 203.

Figure 3:
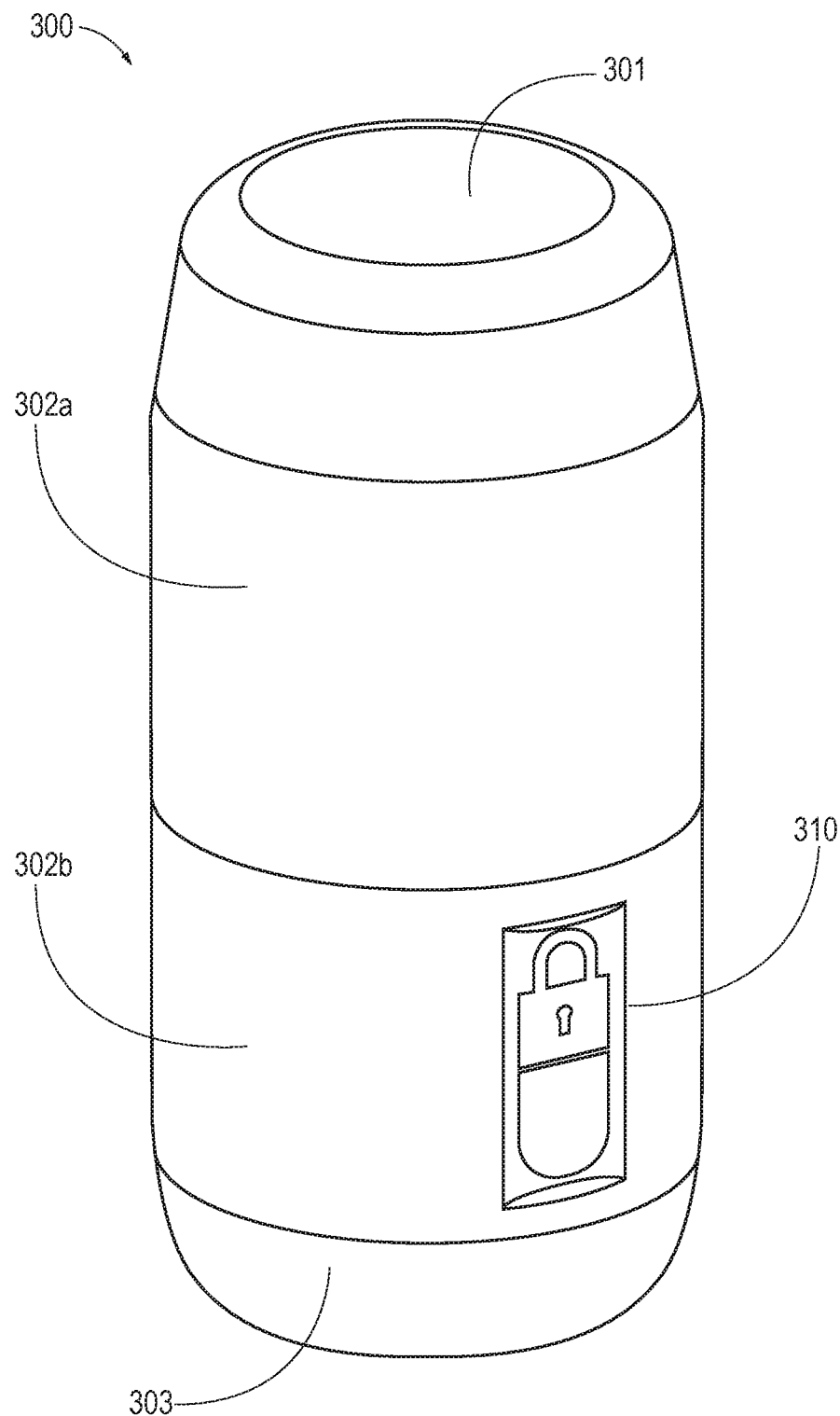
FIG. 3 is an outer perspective view of a container according to one embodiment of the present invention having added capacity as compared to FIG. 2.

FIG. 3 illustrates an alternate embodiment of a container 300 of the present invention. The embodiment of FIG. 3 comprises a lid 301, dual staged body comprising upper stage 302a and lower stage 302b, and a base 303, the lower stage 302b comprising a user authentication means 310 such as a fingerprint scanner for authentication of the user either automatically or by remote means, such as by signaling a custodian having a computing device in communication with a system of the present disclosure of the user authentication of a person seeking access to the medication inside for confirmation via the computing device such as a smartphone in network communication with a web server of the container. The custodian can then transmit unlocking instructions enabling the patient whose identity has been verified to access the contents needed for compliance with dosing instructions, and may be alerted by a vibration sensor of the base (not shown) in the event of an unauthorized access attempt. The embodiment of FIG. 2 may also comprise a USB charging port and Bluetooth transceiver (not shown), such as in the base 303. The dual stage body of the container 300 of FIG. 3 has twice the capacity as the container 200 shown in FIG. 2. One of ordinary skill in the art will appreciate that additional stages may be added for added capacity.

While the embodiments of FIGS. 2 and 3 are equipped with access control features that only allow authorized parties to open the container, e.g., by removing the lid to access the contents inside, they are not equipped with a means of limiting the amount of medication that may be removed from the container by an authorized individual or improving compliance with dosing regimens, such as by providing a daily dispensing means for one or more medications for individuals needing to access medications at specific intervals for compliance. The embodiment of FIG. 4 is that of a controlled dispensing container 400 having additional features for the prevention of overdosing, for example.

Figure 4:
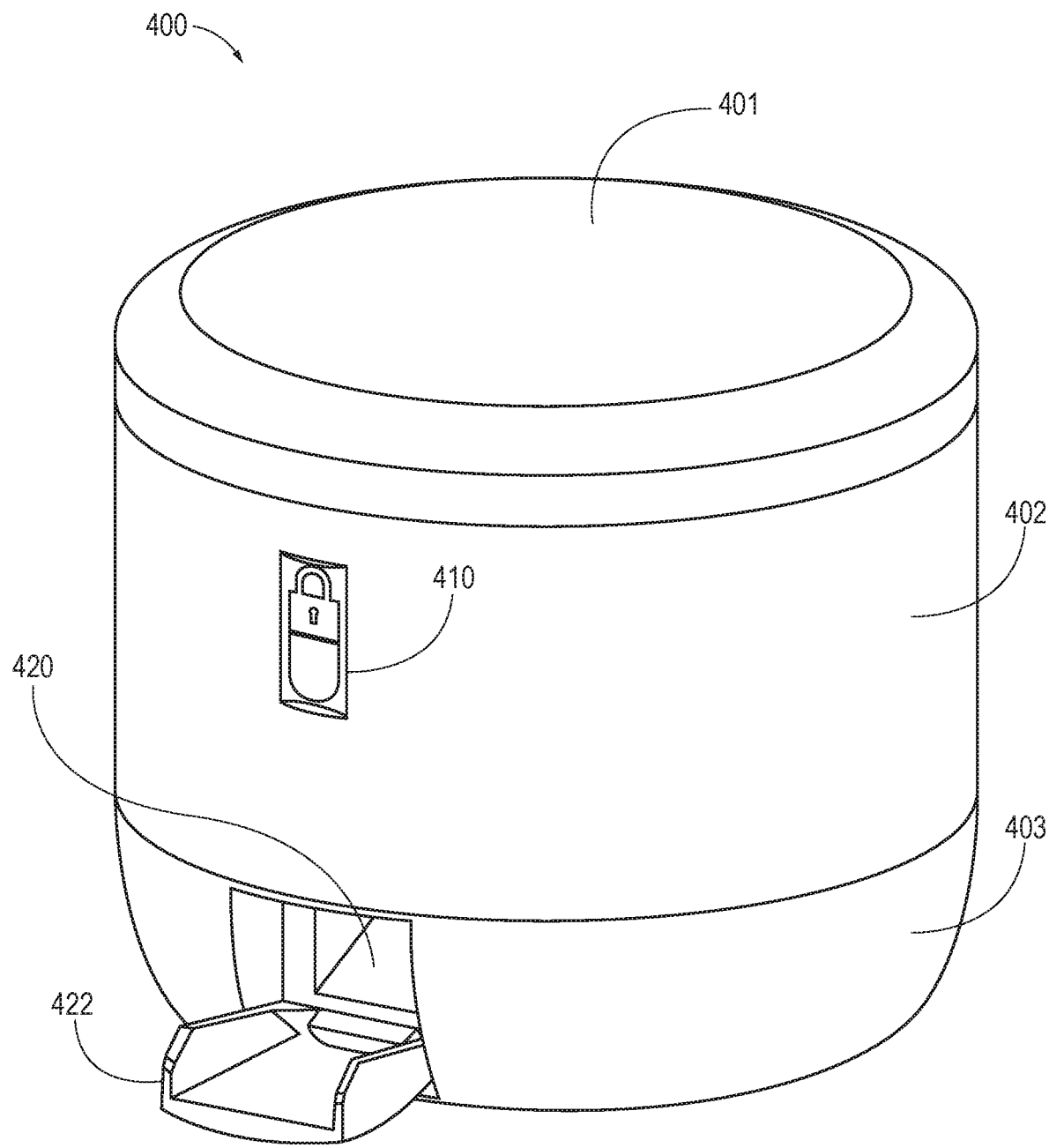
FIG. 4 an outer perspective view of a container according to one embodiment of the present invention having a dispensing means responsive to user authentication.

The illustrative embodiment of FIG. 4 comprises a lid 401, body 402 and base 403, the body having an authentication means such as a fingerprint scanner 410. The embodiment of FIG. 4 further comprises an automatic dispensing means comprising a reservoir 420 and chute 422. When an authorized individual accesses the container by scanning his or her fingerprint or otherwise, the dispensing means is configured to release only that amount of medicine the individual is authorized to receive, based on the time of the latest preceding dose and the amount needed for the next dose. The embodiment of FIG. 4 may also comprise a USB charging port and Bluetooth transceiver (not shown), such as in the base 403.

Figure 5:
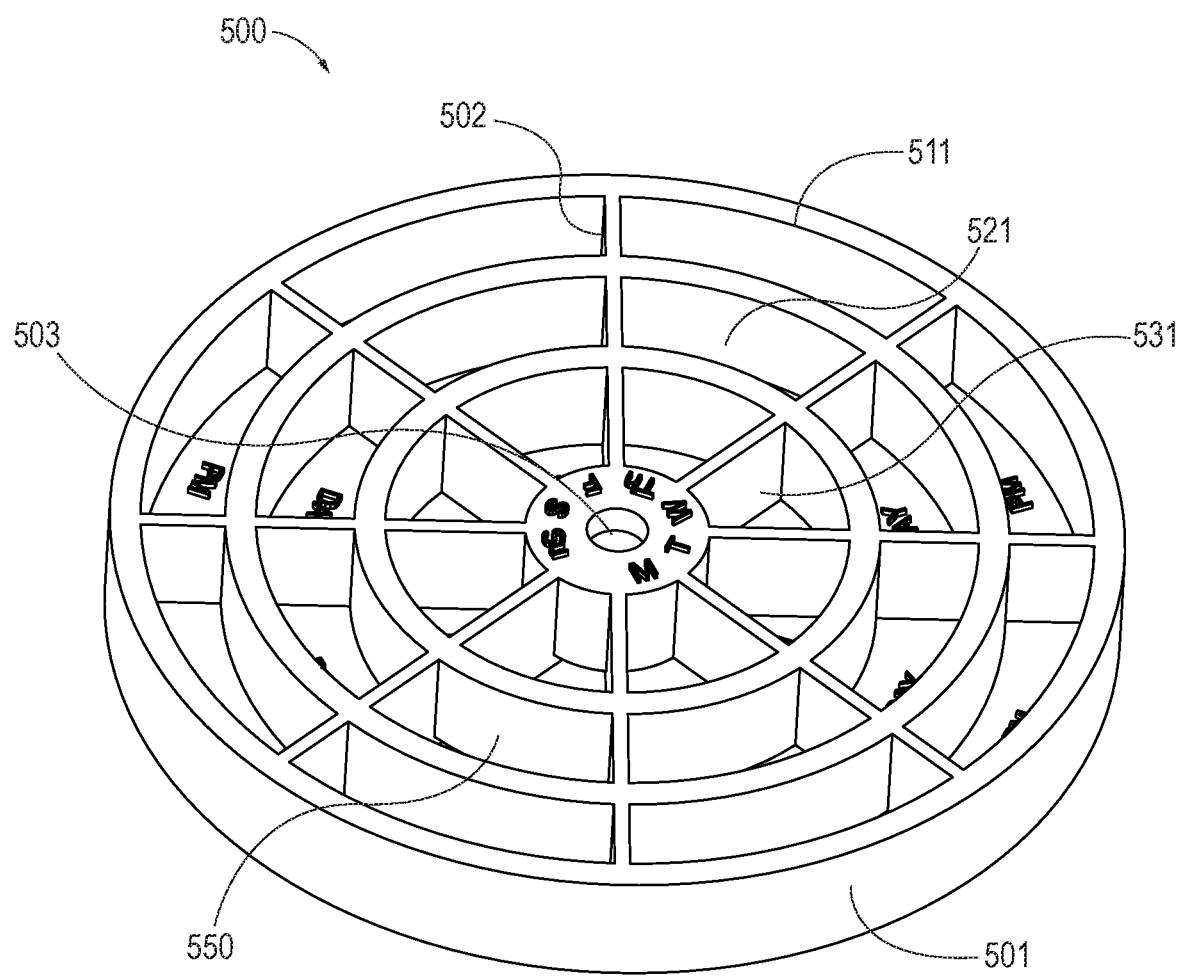
FIG. 5 is a perspective view of weekly pill dispensing wheel suitable for use within a container of the present invention.

Turning now to internal features of certain embodiments of the present invention, FIG. 5 provides a perspective view of a dispensing wheel 500 according to an embodiment of the present disclosure. The dispensing wheel 500 is configured an outer wall 501 and eight dividing walls 502 defining eight pie-shaped receptacles, each comprising an outer cell 511, middle cell 521 and inner cell 531 defined by two concentric inner walls 550 arranged radially around an axis 503 and intersecting perpendicularly with the dividing walls 502. Each pie-shaped receptacle comprises, as a result of this configuration, three internal cells (outer, middle and inner) from which medications can be dispensed, for example, at different times throughout each day. The dispensing wheel 500 illustrated in FIG. 5 is thus suitable for dispensing medications daily for one week, up to three doses per day.

As is illustrated in FIG. 5, in addition to having a pie-shaped receptacle corresponding to each day of the week, an eighth pie-shaped "blank" receptacle is provided which lacks a floor. Each of the inner, middle and outer cells corresponding to each day of the week have floors when in the "starting position" prior to use. As an example, an authorized individual required to take three doses of medication per day—AM, Day and PM for example—may load one or more dispensing wheels 500 into, for example, into an embodiment of a container as described herein as shown in FIG. 4, add the appropriate medications into each dispensing cell, and upon authentication on first use, initiate the rotation of the pie-shaped receptacle corresponding to Monday over the floorless position, thereby releasing the medication to be taken on Monday morning through a subfloor having an opening in vertical alignment with the inner cell 531 into the reservoir 420 and opening the chute 421, enabling the user to receive the medication for that time. Following the next successive authentication, the subfloor rotates, exposing a portion of the subfloor having an opening in vertical alignment with middle cell 521, resulting in the release of medication in the middle cell 521 into the reservoir 420 and chute 421, and so on. In this way, the individual may only receive the proper dosage at the proper time, assuming the dispensing wheel is loaded correctly.

In certain embodiments, internal motors work in tandem to rotate the individual wheels, and the bottom disk attached per wheel, contained within the outer housing of the device. These motors will enable the container to use gravity to its advantage. The motors will rotate an open slot to align open columns throughout all stacked wheels to enable the medication to fall from any of the stacked wheels to the reservoir.

Figure 6:
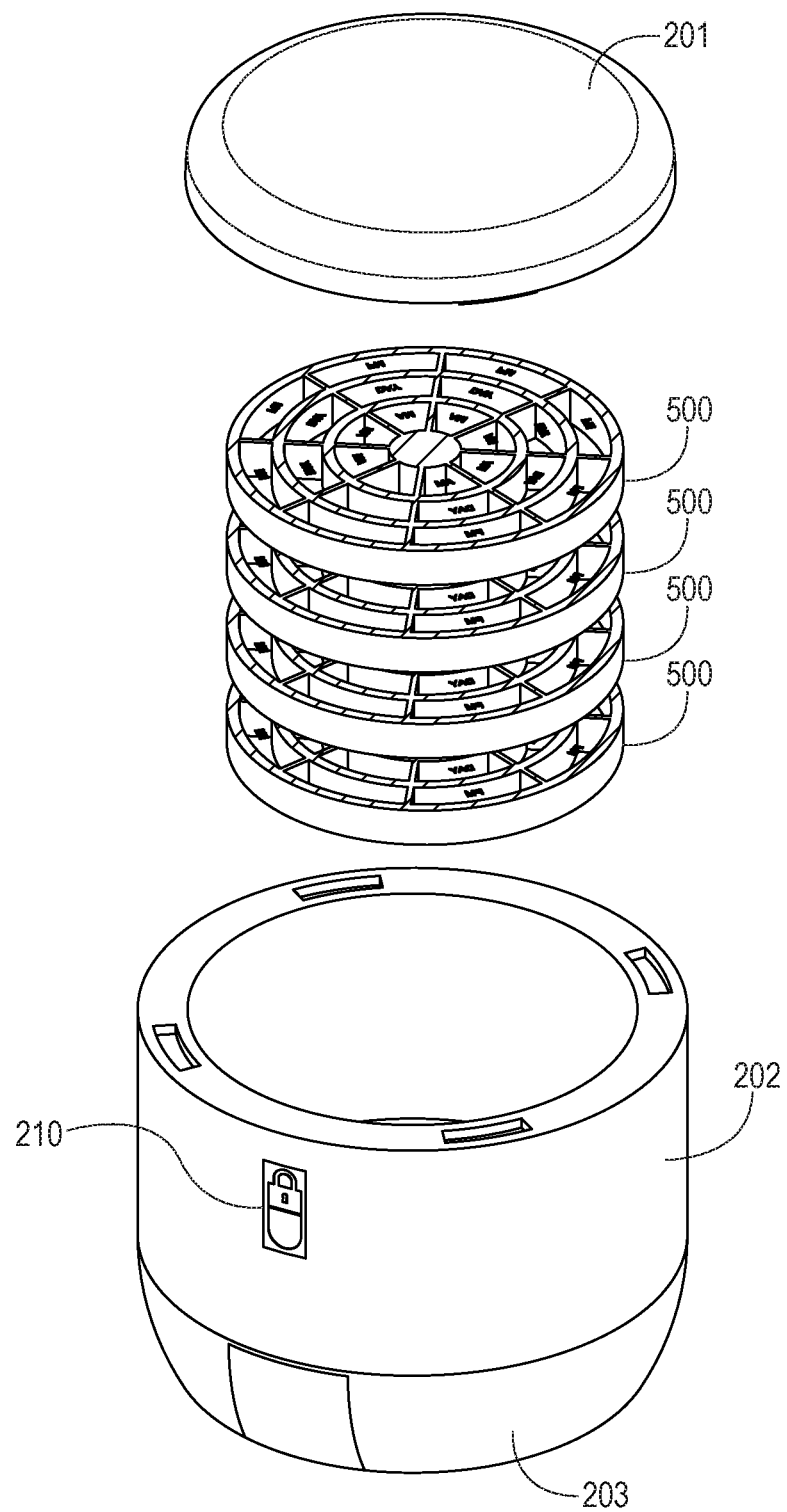
FIG. 6 is an exploded view of a container according to an embodiment of the present invention, with stacked weekly distribution wheels shown that are internal within the container when closed.

In the embodiment illustrated in FIG. 6, four distribution wheels 500 are shown as being stacked vertically within a container as shown in FIG. 2. This embodiment lacks the dispensing means illustrated in FIG. 4, but enables a more reliable user to authenticate at the fingerprint scanner 210, causing an unlocking of the lid 201 from the body 202, exposing the uppermost dispensing wheel 500 so the user can remove the medication he or she needs manually. As one of ordinary skill in the art will appreciate, the security feature of embodiment 200 is a key object of the embodiment, while FIG. 4 illustrates an embodiment 400 where security and compliance are both key objects of the invention. One of ordinary skill in the art will understand based on this description that various durations of compliance may be achieved depending on the number of dispensing wheels 500 stacked throughout a container of the present disclosure, such as 28-day compliance as is an object of the exemplary embodiment of FIG. 6.

Figure 8:
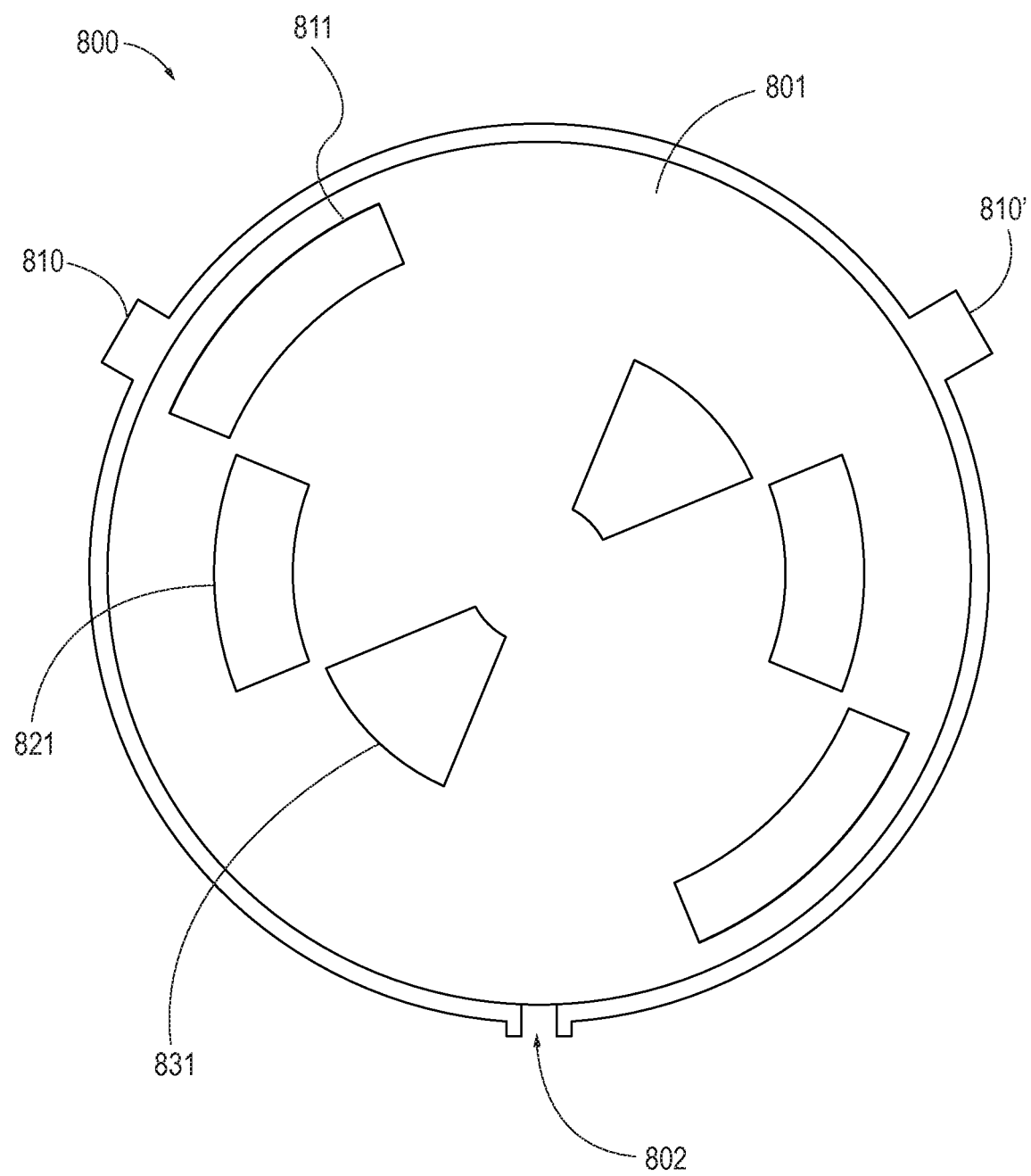
FIG. 8 illustrates the bottom floor of an exemplary dispensing wheel arrangement, as shown for example in FIG. 6.

Considering FIG. 8 in view of FIG. 6, an exemplary subfloor assembly 800 of a dispensing wheel arrangement such as that according to FIG. 6 including subfloor 801 is illustrative of the workings of the inner container components. The subfloor 800 of FIG. 8 includes subfloor openings 811, 821 and 831 that may be set in alignment with outer cells, middle cells and inner cells, respectively, when medicine contained in those cells is to be dispensed. Subfloor tabs 810 and 810', along with subfloor receiver 802 interact with gears or equivalent mechanical components to facilitate the appropriate rotation of the subfloor assembly 800 to position subfloor openings 811, 821 and 831 appropriately to allow for the passing through of medications into a dispensing reservoir such as that shown in FIG. 4 as 420. The complimentary rotations of dispensing wheels and subfloor enables versatile medication dispensing according to any desired schedule. One of ordinary skill in the art will understand that the subfloor may be configured with fewer or more openings corresponding to fewer or more dispensing cells such as those first described in FIG. 5 in order to accommodate multiple dosing schedules, and the parts may even be made interchangeable.

The advantages of a tamper-resistant container as described herein include, without limitation, significant reduction in the ability to tamper with or break into the container and steal controlled substances or illegally access prescription medication, automatic notification to the owner if a break-in attempt occurs, simplicity of access for the content owner, and accessibility and data tracking via a computer software application, preferably accessible from a mobile computing device. Future enhancements over the current state of the art include, but are not limited to the use of a fingerprint scanner, for example, which may already be accessible by mobile phones and the like; integration of video, audio, camera and global positioning system (GPS) functions; automatic transmission of reminders when to take medication and warnings on side effects; and integration with Internet of Things (IoT) type devices; live results from wearable health monitors and sensors; alerts of drug interactions and lock out periods based on instructions for administration; and interfaces with available pharmaceutical prescription information, dispensing guidelines and directions of when to take the medication. The final shape, size, weight and dimensions of the invention may be customized through developmental, operational and user testing. In the event a patient is locked out of his or her medicine container, accidentally, due to a system malfunction, or as a result of proper system function, a physical key may be provided to enable access.

Figure 7:
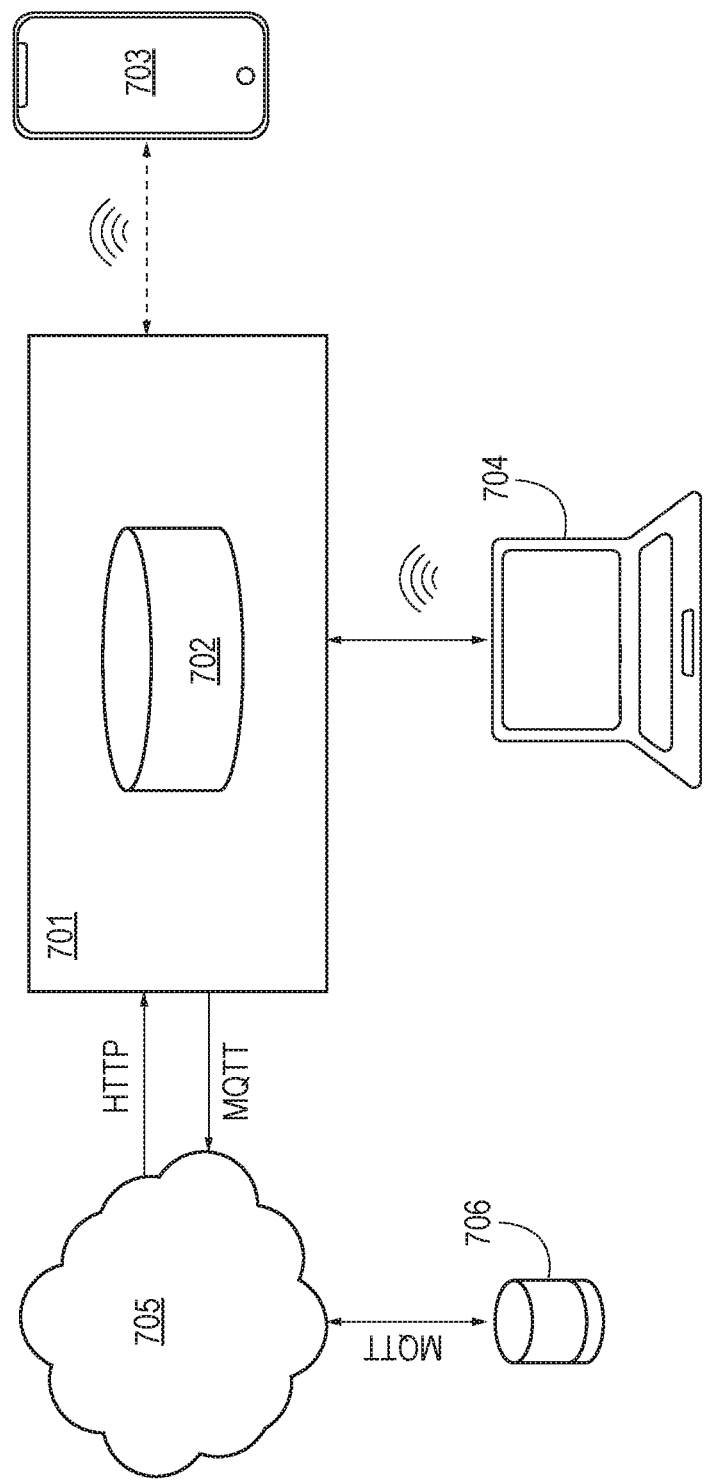
FIG. 7 illustrates an exemplary system architecture for enabling the container features described herein and the claimed methods.

The invention of the present disclosure further comprises a system as represented in FIG. 7. In this exemplary embodiment, a web server 701 in network communication with a cloud server 705 via Hypertext Transfer Protocol (HTTP) (incoming) and Message Queuing Telemetry Transport (MQTT) protocol (outgoing), the cloud server 705 being in wireless communication with a tamper-resistant container according to the present disclosure via MQTT. A smartphone 703 configured with an API for interaction with a computer software application tangibly stored on a non-transitory computer readable medium, such as but not limited to a web server 701 or cloud server 705. Data inputs from the smartphone 703 are processed according to the instructions contained in the software application by a microprocessor in network communication with the cloud server 705, for example. Processing includes but is not limited to user authentication, locking or unlocking of the container, or alerting or messaging the smartphone. The system is designed to anonymize all data traffic to and from a container as described herein, thereby maintaining the data privacy of individual users of a system comprising a container as described herein. Data collected and stored within a system of the present disclosure may be stored on a database 702 and related to the utilization of a container as described herein to enable analytics on users. In addition to the medication specific updates, a software and container combination as described herein may be applied to protecting contents other than medications, such as alcohol, weapons, artwork and any other contents people wish to protect and guard against unauthorized access. Updates can be pushed out to the web server 701 using any suitable computing means 704.

Users of a system as described herein determine who should have access to the system and set permissions according to their role as user, custodian, physician, etc. Users may input information on medications, dosages, dosage regimens and so forth to better manage adherence to prescription requirements. In preferred embodiments, a container according to the present invention may hold up to four weeks of medication schedule to be dispensed at least up to three times per day, although this is by way of example and not limitation. A system of the present disclosure may be configured to interface with pharmacies through tele-health programs to enable seamless refilling and delivering of medications prior to running out.

In certain embodiments, a system of the present invention also may provide guided medication adherence instructions for custodians or individuals taking medications. These may be communicated via audiovisual means over a computing means such as a smartphone. It is an object of the present invention to teach better medication adherence to individuals who suffer from disabilities such as autism or attention deficit disorder who may have difficulty focusing on proper adherence.

Specific embodiments of the present invention comprise a tamper resistant pill bottle, case and lid with unique identity authentication and mobile locking, unlocking and alarming capability, integrated into a system comprising a computer software application accessible via a smartphone or physically located on the bottle, case or lid. Future enhancements will be made based on system testing along with user input and feedback.

While the foregoing written description of the invention enables one of ordinary skill to make and use what is considered presently to be the best mode thereof, those of ordinary skill in the art will understand and appreciate the existence of variations, combinations, and equivalents of the specific embodiments, methods, and examples described herein. The invention should therefore not be considered limited according to the illustrative embodiments described herein, but by all embodiments and methods within the scope and spirit of the invention as claimed.

What is claimed:

1. A system for preventing unauthorized access to medications, the system comprising:
   a tamper-resistant container of durable construction, the container further comprising:
   at least one internal dispensing means for dispensing medications at predetermined intervals and dosages to an individual, each dispensing means comprising a plurality of cells each comprising a plurality of sub-cells, wherein all but one of the cells has a floor, wherein each of the sub-cells is configured to rotate to a position without a floor, causing its contents to fall out into a first reservoir beneath within a predetermined period of time after the identity of the individual is authenticated, wherein a chute connected to the reservoir opens in turn, enabling the individual to access the medications, or causing its contents to fall out into a second reservoir beneath after the predetermined period of time has lapsed;
   an identifier capable of obtaining identity authentication data personal to the individual seeking access to medications contained therein;
   a transceiver configured to wirelessly transmit data to a cloud server and a power source, wherein upon obtaining the identity authentication data the transceiver transmits the identity authentication data to a cloud server in communication with a web server comprising at least one database and software program instructions tangibly stored thereon, which when executed cause a processor to authenticate the identity of the individual based on the authentication data and either permit the individual to access the medications upon authentication or request permission to access the medications from another person.

2. The system of claim 1, further comprising a computing means configured with a software application and application programming interface in wireless communication with the web server, wherein the other person may grant or deny the individual access to the medications by sending instructions to the web server through a user interface installed on the computing means over the API.

3. The system of claim 2, further comprising a means for updating the software instructions.

4. The system of claim 3, wherein the transceiver is configured to send and receive information from the cloud server using Message Queuing Telemetry Transport (MQTT) protocol.

5. The system of claim 3, wherein the cloud server is configured to transmit data to the web server using MQTT and receive information from the web server using Hypertext Transfer Protocol (HTTP).

6. The system of claim 3, wherein the identity authentication data represents a biometric identifier of the individual.

7. The system of claim 3, wherein the transceiver is a Bluetooth transceiver.

8. The system of claim 3, wherein the container further comprises a vibration sensor.

9. A method of controlling access to medications, the method comprising providing a system according to claim 1 and dispensing the medications only after authentication of the identity of the individual.

10. A method of authorizing a refill of prescription medications, the method comprising providing a pharmacy telehealth system with access to a system according to claim 1, wherein the pharmacy telehealth system authorizes the medication refill, loading and transport in response to administration data supplied from the system according to claim 1 and the system further comprises a means for tracking compliance with refill regulatory requirements.

11. The system of claim 1, further comprising a locking mechanism for preventing unauthorized access to the medications.

12. The system of claim 2, further comprising an access detection sensor of the tamper-resistant container, wherein the other person may detect access to the medications via the web server through a user interface installed on the computing means.

13. The system of claim 12, wherein the access detection sensor is configured to detect and log access attempts to the container and allow access to the container only when the identity of the individual seeking access is authenticated.

14. The system of claim 13, wherein the access detection sensor is configured to notify the owner of the container when the identity of the individual seeking access is not authenticated, wherein the owner can permit or block access based on the notification.

15. The system of claim 1, further comprising a computing means configured with a software application and API in wireless communication with the web server, wherein the software application comprises instructions which when executed by a processor cause the processor to track adherence to a medication schedule of a person accessing medications using the system and reward the person with a video game for adherence.

16. The system of claim 13, wherein the individual accessing medications is selected from the group consisting of persons suffering from addiction, persons suffering from intellectual or developmental disabilities or any person requiring medication or supplements.

17. The system of claim 2, wherein the other person may log the impacts of the medications on the individual accessing the medications by entering impact information into a database of the web server through a user interface installed on the computing means.

* * * * *